(12) United States Patent
Rees

(10) Patent No.: US 6,689,317 B1
(45) Date of Patent: Feb. 10, 2004

(54) IMMUNOASSAY APPARATUS FOR DIAGNOSIS

(75) Inventor: John Rees, Llandudno (GB)

(73) Assignee: Clinical Diagnostic Chemicals Limited, Pendraw'r Llan (GB)

(*) Notice: Subject to any disclaimer, the term of this patent is extended or adjusted under 35 U.S.C. 154(b) by 0 days.

(21) Appl. No.: 09/440,787

(22) Filed: Nov. 15, 1999

Related U.S. Application Data (63) Continuation-in-part of application No. PCT/GB98/01412, filed on May 15, 1998.

(30) Foreign Application Priority Data

May 15, 1997 (GB) .............................................. 9709821

(51) Int. Cl.⁷ .............................................. G01N 31/22
(52) U.S. Cl. ........................ 422/58; 422/100; 422/103
(58) Field of Search ............................ 422/100, 103, 422/58; 436/169, 170, 514, 807

(56) References Cited

U.S. PATENT DOCUMENTS

| | | | |
|---|---|---|---|
| 4,960,691 A | | 10/1990 | Gordon et al. |
| 5,198,193 A | * | 3/1993 | Bunce et al. ............... 422/100 |
| 5,275,785 A | * | 1/1994 | May et al. .................... 422/56 |
| 5,308,775 A | * | 5/1994 | Donovan et al. ........... 436/518 |
| 5,770,460 A | * | 6/1998 | Pawlak et al. .............. 436/510 |

FOREIGN PATENT DOCUMENTS

| | | |
|---|---|---|
| DE | 40 37 724 A1 | 6/1991 |
| EP | 0186 799 | 7/1986 |
| EP | 0 314 499 | 10/1988 |
| EP | 0 590 695 A2 | 3/1990 |
| GB | 2 231 150 | 11/1990 |
| GB | 2 261 283 | 5/1993 |
| GB | 2 261 284 | 5/1993 |
| GB | 2291283 | 1/1996 |
| WO | PCT/EP94/04232 | 12/1994 |
| WO | PCT/ES96/00042 | 1/1996 |
| WO | WO/ 96/24060 | 8/1996 |

* cited by examiner

Primary Examiner—Jill Warden
Assistant Examiner—LaToya Cross
(74) Attorney, Agent, or Firm—Gordon & Jacobson, P.C.

(57) ABSTRACT

Immunoassay analytical test apparatus for allergy diagnosis, which apparatus comprises a zone for receiving a sample containing an analyte, a zone for receiving a mobile phase (the zone may be the same as the sample receiving zone, or different thereto), a detection means for permitting detection of the analyte by immunoreaction, a first flow path for flow of the analyte in the mobile phase from the sample receiving zone to the detection means, and a second flow path permitting flow of a mobile phase to the detection means.

10 Claims, 3 Drawing Sheets

IMMUNOASSAY APPARATUS FOR DIAGNOSIS

CROSS-REFERENCE TO RELATED APPLICATION

The present application is a continuation in part of international application PCT/GB98/01412 filed on May 15, 1998 by the same applicant as the present invention.

BACKGROUND OF THE INVENTION

The present invention relates to apparatus for the diagnosis of allergies. In particular, the invention relates to immunoassay apparatus that does not require sophisticated laboratory equipment or technical expertise and is suitable for use in the home or the doctor's surgery.

A number of kits using immunoassay technology (mainly for pregnancy testing or fertility prediction) are widely available for use in the home or in a doctor's surgery. The format of the immunoassay technique in such kits is broadly similar, utilizing test strips containing immobilized immunoreactant and requiring the user to provide and apply a sample of a predetermined body fluid. Some devices that use urine as the source of the analyte require no further intervention than the application of the sample to the device. This is an ideal situation where urine not only contains the analyte but also acts as the fluid component of a mobile phase which initiates the chemical reaction within the device.

However, other samples may not be readily available in such copious volumes. For applications where urine is not appropriate, a blood sample is usually required, although other body fluids may also be of use, for example, saliva or tears. Due to practical and ethical reasons, devices that are designed for use in the home and that require a blood sample must work with a capillary sample not usually larger than a few hundred microliters in volume.

For most devices, because of physical constraints such as flow properties, this volume is insufficient to initiate the chemical reaction and permit it to proceed. Additional fluid components must then be added to the kit in order to provide a mobile phase. This mobile phase can be contained within a compartment inside the apparatus, the release of which is initiated either by physical intervention by the user, or by a chemical interaction of the sample with a physical barrier separating the mobile phase from the immunoreactants. The mobile phase could also be added from a separate container to a receptacle on the device itself. Of course the more steps that are involved with the operation of the kit, the more chance there is for error by the user and less is the likelihood of obtaining a correct result.

For some medical conditions, it is important to obtain a rapid test result. For example, a result within minutes of sample application may be required with a test to be used in emergency situations, whereas for other conditions a result within minutes may not be necessary.

Currently available apparatus is often non-sequential in nature, meaning that the reaction involves a single step. However, one of the main problems with non-sequential immunometric test kits is the occurrence of a phenomenon called a "high dose hook effect". The high dose hook effect is evident when high levels of antigen in the system saturate the assay. This is caused by free analyte being left in the sample after reaction of all the available labelled immunoreactant and the inadequate binding capacity of the immunoadsorbent for the amount of complexed and free analyte in the system. This unlabelled analyte can then compete downstream for the immobilised immunoreactant. In some cases, when there is a large amount of analyte in the sample, false negative results can be obtained merely because of saturation of the labelled immunoreactant and immunoadsorbent. These false negative, or abnormally low, results may influence decisions on treatment made by the user or clinician. This will not occur if sufficient immunoadsorbent is present. However, there are limitations to the binding capacity of an immunoadsorbent, and it is not generally practical to increase the amount of labelled immunoreactant in the system to overcome the high dose hook effect, as this will tend to increase the non-specific binding of the labelled immunoreactant, thereby reducing the analytical sensitivity of the assay, giving rise to an elevated reference (blank) reading. In conventional laboratory immunoassays, this problem is overcome by carrying out a sequential assay, with discrete wash steps between each addition of sample and immunoreactant. Sequential immunometric assays can be easily run in a laboratory. For example, a sample which contains analyte may be allowed to react with an immobilized immunoreactant specific for the analyte in question. After a predetermined incubation period, unbound analyte in the sample may be washed away, usually by a combination of decantation and washing. Then the labelled immunoreactants are added.

A further method to circumvent the high dose hook effect, and to avoid the sequential format, would be to use a competitive assay format. However, this is not ideal. For example, with such assays, the precision is highly dependent on the region of the dose response curve being examined. In contrast to immunometric assays, the response in competitive assays is inversely proportional to the dose—that is, a lower signal is obtained with higher concentrations of analyte. In general, this is not a preferred attribute for a home testing kit where the absence of a signal confers a positive result. A preferred way to avoid the high dose hook effect while maintaining an acceptable assay format is a sequential immunometric assay approach. However, the requirement for separate addition of reagents by the user and intervening discrete wash steps, would make such a testing device too cumbersome for home or office use.

EP 0314499 A discloses a test device for carrying out an immunoassay and making a color change result visible to the user. The device comprises a first "fast" flow path and a second "slow" flow path of porous or fibrous liquid conductive material. The ends of both tracks are contacted with a sample liquid store (mobile phase containing the analyte). The first path for flow of the analyte contains an enzyme and the second path contains a labelling substrate corresponding to the enzyme. Both paths lead to a detection means.

EP 0186799 A discloses an analytical device comprising a zone for receiving sample containing an analyte, a zone for receiving the mobile phase and a detection zone. The document teaches the possibility of having two parallel flow paths which start from the mobile phase reservoir and lead the detection zone, wherein the main path transports the sample containing the analyte and the second path entrains reagents for color detection.

EP 0590695 A discloses a liquid transfer device for use in assay procedures, comprising a sheet of porous material for capillary liquid flow therethrough. The sheet is formed to define two liquid flow channels leading from two channel ends to a site in a common channel portion, where the two channels merge. The two channels are operable to deliver liquid to said common site in a sequentially timed manner following simultaneous application of such liquid to the channel ends.

OBJECTS OF THE INVENTION

The present invention aims to overcome the problems associated with non-sequential immunometric assays by providing a selfdiagnosis apparatus which can use a sequential immunoassay method, but which does not require sophisticated laboratory equipment or technical expertise.

It is an object of the present invention to provide a self diagnosis apparatus utilising immunoassay technology which is particularly useful for the measurement of antigen-specific human immunoglobulin E (IgE), as in allergy diagnosis, but which may also be used for other analytes and isotypes.

SUMMARY OF THE INVENTION

Immunoassay analytical test apparatus for allergy diagnosis according to the present invention comprises:

(a) a zone for receiving a sample containing an analyte;

(b) a zone for receiving a mobile phase, which zone may be the same as the sample receiving zone, or different thereto;

(c) a detection means for permitting detection of said analyte by immunoreaction;

(d) a first flow path for flow of said analyte in said mobile phase from said sample receiving zone to said detection means; and (e) a second flow path permitting flow of said mobile phase to said detection means.

It is a preferred feature of the present invention that the second flow path includes therein labelled immunoreactive material capable of reacting with the analyte to produce labelled anylate.

It is a preferred feature of the present invention that the first flow path includes unlabelled or hapten labelled (such as biotinylated) immunoreactive material being placed upstream and/or downstream of the sample receiving zone. It is a further preferred feature that the first flow path includes both unlabelled or hapten labelled capture material and detector labelled material. The materials may be dried onto the flow path substrate upstream and/or downstream of the sample receiving zone. As the mobile phase containing the analyte flows towards the detection means the dried material may be solubilized by the mobile phase.

The problems associated with non-sequential immunometric assays may be alleviated by permitting the analyte to reach the detection means, where it is immunoextracted by an immunoadsorbent, before a substantial amount of labelled immunoreactive material reaches the detection means.

According to a first embodiment of the present invention this may be achieved by providing detection means which may be separable from the flow paths, thereby allowing the detection means to be moved from the flow path comprising the analyte to the flow path comprising labelled immunoreactive material only after sufficient immunoadsorption of the analyte in the detection zone has taken place.

Therefore, according to a first embodiment of the present invention the test apparatus comprises:

(a) a zone for receiving a sample containing an analyte;

(b) a zone for receiving a mobile phase;

(c) a first flow path for flow of an analyte in said mobile phase from a sample receiving zone to a detection means;

(d) a second flow path for flow of a mobile phase from a mobile phase receiving zone to detection means, said flow path having therein a zone containing labelled immunoreactive material capable of reacting with said analyte to produce labelled analyte; and wherein the detection means is movable from a first position in communication with said first flow path to a second position in communication with said second flow path.

It is a preferred feature of the first embodiment of the present invention that the detection means is movable to be in communication with the first and second flow paths in sequence. It is further preferred that there is contact between the detection means and the first and second flow paths.

The flow paths according to the present invention comprise elongate sheet or strip material having a portion connectable with said first and/or said second flow path. The flow paths are designed to potentiate flow toward the detection means by permitting movement of mobile phase in a longitudinal direction.

According to a second embodiment of the present invention the arrival of the labelled immunoreactive material to the detection means may be delayed by having a longer flow path for the labelled immunoreactive material relative to the flow path for the analyte.

Therefore, according to a second embodiment of the present invention, the test apparatus comprises:

(a) a zone for receiving a sample containing an analyte;

(b) a zone for receiving a mobile phase, which zone may be the same as the sample receiving zone, or different thereto;

(c) a detection means for permitting detection of said analyte by immunoreaction; and (d) first and second flow paths for flow of said analyte in said mobile phase from said sample receiving zone to said detection means, said second flow path having therein a zone containing labelled immunoreactive material capable of reacting with said analyte to produce labelled analyte, such that unlabelled analyte reaches said detection zone via said first path before said labelled immunoreactive material reaches said detection zone via said second path whereby said labelled immunoreactive material can react with immobilized analyte.

According to the second embodiment of the invention, it is preferred that the flow paths are such that the mobile phase is allowed to traverse more than one route simultaneously. The first and second flow paths are preferably both continuous from the mobile phase receiving zone to the detection means. The most direct route of the mobile phase is through the sample receiving zone and into the immunoadsorbent. However, simultaneously, the mobile phase can also travel along a different conducting element. Within this alternate route the mobile phase passes through a zone of labelled immunoreactant which is free to move in the conducting element when in the moist state only. This alternate path of mobile phase carrying the labelled immunoreactants also leads to the immunoadsorbent.

The immunoassay apparatus according to the present invention preferably comprises an external body and an internal body. The external body typically includes a receptacle for the addition of a sample containing the analyte, and a compartment where the result of the test can be observed.

Furthermore, the external body of the apparatus may comprise a lancet to enable the user of the device to provide a blood sample. The lancet may be integrally molded to the external body of the apparatus, or it may be provided separately.

Furthermore, a desiccant tablet may also be included in the apparatus and the entire unit hermetically sealed to prevent deterioration through humidity changes. The apparatus is particularly suited for use in the home, at a patient's bedside or in a doctor's office.

A further embodiment of the device is the inclusion of a recess into the external body of the apparatus to which a drop of blood is added. It is preferred that this recess leads directly to the surface of the first flow path. The recess may be arranged to prevent the user touching the surface of the flow path during the course of the test.

All the components necessary to obtain a result, except for the sample containing the analyte to be detected, may be provided as a kit and therefore the use of the apparatus according to the invention is not limited to the laboratory.

To operate the apparatus according to the present invention, a user provides a sample containing the analyte, for example, a sample of blood. A capillary blood sample can be taken using a lancet (which is preferably incorporated into the apparatus) to prick a finger. The blood or other sample is then allowed to be taken up by a sample receiving zone. The sample receiving zone preferably comprises a suitable blood filter to aid separation of plasma from the whole blood sample. Mobile phase may then be applied upstream of the sample.

Aliquots of mobile phase may be applied indirectly to the mobile phase receiving zone from a separate container holding mobile phase, for example, from one or more dropper bottles. The mobile phase, in this case, would be applied onto an adsorbent solid phase which is a continuation of the body of the testing apparatus, or it may be applied in the form of a well with a connecting chamber to the sample application zone and other conducting elements. Alternately, the mobile phase, which typically comprises physiological saline and antimicrobial preservatives, may be released into the apparatus directly from an integrated reservoir. In this case, the mobile phase may be contained within a blister or the like, permitting release of the mobile phase during operation of the apparatus. The mobile phase may be released by applying pressure or, for example, by suitable piercing means, to the surface of the blister causing the blister to be punctured. The piercing means may be incorporated into the apparatus. Once punctured, pressure on the top of the blister causes deformation of the blister thereby squeezing out the mobile phase from the blister. Alternately, the direct release of mobile phase may be by chemical intervention. The chemical intervention may be initiated by compounds in the sample acting to "digest" a membrane, thereby releasing the contents of a reservoir for the mobile phase. No further intervention is required by the user except to read the result of the test, a positive result being indicated by color in the detection zone, after a predetermined incubation time.

As previously mentioned, the present invention is particularly suitable for use at home or in the doctor's surgery. It is therefore impractical to obtain a blood sample greater than a few hundred $\mu l$ in volume, a preferred volume being less than 50 $\mu l$. This volume of whole blood is roughly 50% cellular which normally leaves less than 20 $\mu l$ of liquid sample available for analysis. Allergy tests have to be highly sensitive to detect minute amounts of IgE present in the circulating blood. It is therefore advantageous to extract as much of the plasma into the test system as possible. A system that uses the sample as a source of mobile phase for the labelled immunoreactant and subsequent wash steps of a sequential immunoassay is therefore impractical for the minute volumes available in this instance. Here a separate mobile phase is added from a reservoir that pushes the plasma out of the sample laterally through the filter.

Advantageously, it is this lateral separation rather than transverse flow of the capillary blood sample through a suitable filtration means (which may advantageously comprise the material of the first flowpath) which results in the efficient extraction of plasma components free of red cells. The mobile phase pushes the plasma component out of the sample causing the plasma to travel laterally along the length of the flow path (rather than causing separation through the depth of a filter in a conventional manner which would cause a significant fraction of the plasma to be retained). The sample, free of cells, is drawn laterally through the flow path by the addition of a mobile phase, which may also contain labelled reactants, towards the immunoadsorbent. This is in contrast to single step devices in which the immobilized reactants nearest to the application zone are exposed to more of the analyte than immobilized reactants more distal to the application zone.

In a preferred embodiment of the present invention, the apparatus additionally comprises a blood filter. A sample of whole blood (typically approximately 50 $\mu l$) may be applied to the surface of a suitable cell filter, for example, a CytoSep filter (Ahlstrom filtration) or a glass fiber filter such as GF/A (Whatman), or GF51 (Schleicher and Schuell) which may be pre-treated with detergents, anticoagulants and other reagents common in immunoassay technology. The receptacle housing such a filter protects the user from the chemical and allergenic contents of the apparatus. The filter may contain a chemical anticoagulant such as oxalate or fluoride, a chelating agent (such as EDTA) or an anticoagulant such as heparin. Some cells may also be removed by specific binding agents immobilized close to the sample application zone, such as polyfunctional group reactive lectins. The cells could also be lysed by physical or chemical shock, such as by change in the pH or ionic environment, freezing, heating, desiccation or the action of specific biological lysing agents or organic compounds. However, for some analytes, removal of the cells will not be necessary for the successful use of the apparatus according to the invention.

Once a sample of blood or the like has been fully adsorbed, the plasma may be separated from the cells by allowing the free end of the filter to come into contact with a solution containing anti-human IgE, which may be hapten or directly labelled, together with preservatives and stabilizers (common to the practice of immunoassay development used to minimise non-specific interactions). However, the use of an anti-human IgG may be useful when diagnosing food allergies that are not dependent on IgE mechanisms. If an indirect label is added at the above step, then a second reagent reactive with labelled groups on the anti-IgE or anti-IgG antibody can be added by simply exposing the free end of the filter to a reagent containing the labelled second antibody. The latter method thereby increases the sensitivity of the detection method. After a predetermined time, the immunoadsorbent will display a fingerprint of the allergic profile of the patient as a series of bands which can be attributed to the existence of allergen specific IgE or IgG antibodies, hence suggesting the possibility of IgE/IgG mediated allergic reactions against those allergens tested.

Referring specifically to the embodiment described with movable detection means, the mobile phase may be absorbed simultaneously along two separate paths leading from the mobile phase receiving zone. The sample receiving zone may comprise a blood filter. This will allow lateral separation of the plasma from the cells and subsequent flow of the plasma into the detection means. After a fixed time, typically 10 minutes, the plasma component of the blood sample will have been extracted from the blood sample and passed through to the detection means, followed by a mobile phase which has the effect of removing free unreacted analyte in the plasma from the detection means.

The blood filter may additionally contains additives for the specific removal of non-IgE isotypes from the plasma. As the plasma sample from a positively testing subject may contain antibodies directed against the allergens in the detector zone, other than allergen specific IgE (which condition may be quite marked in patients with food allergies) there will be a tendency for the IgG antibodies, for example, in the plasma sample, to swamp out the binding of the IgE antibodies against the allergen. This could result in a false negative result being reported for the plasma sample due to inhibition of the test by non-IgE antibody isotypes. Here much of the plasma, and hence analyte, passes through the blood filter that aids removal of the non-IgE antibodies. The means for removal of non-IgE components may comprise ion-exchange material that allows IgE antibodies to pass through unaffected but binds to the non-IgE isotypes preventing their entry into the detection means.

The matrix or filter for the removal of non-IgE components may be provided separate from the blood filter. The blood filter and/or the matrix for removal of non-IgE components are preferably located between the sample application zone and detection means.

An important embodiment of the apparatus according to the invention which increases the specificity of the diagnostic test is that the sample, for example for measuring allergen specific IgE, may be adsorbed free of non-IgE isotypes by passing the sample through a matrix containing an adsorbent reactive with human IgG, IgM or IgA e.g. lectins, protein A or anti-human antibodies, other than the specific antibodies used, thereby facilitating the adsorption of non-specific isotypes (for measurements of IgE, IgD, and IgA or IgG subclasses). Incorporation of an adsorption matrix between the sample application zone and the immunoadsorbent will yield more specific and sensitive allergy assays by excluding interference with non-IgE antibodies. Alternately, the matrix may be provided in the sample application zone within the blood filter. Alternately, the matrix is provided separate to the blood filter. It is also possible to immobilize antibodies to provide a zone in the detection means prior to the allergen impregnated means. For example, the presence of large quantities of non-IgE anti-allergen antibodies in the sample will inhibit the binding of IgE antibodies by competition for the allergosorbent, giving the possibility of a false negative result which may be particularly important for the diagnosis of food allergy mediated by IgE, or where patients have undergone immunotherapy with allergen extracts (which may result in the elevation of non IgE immunoglobulin isotypes). It would therefore be expected that an assay using the apparatus according to the invention would classify some patients as reacting positively to certain allergens, while other commercial allergy assays may have classified as negative or as a lower allergy class. This may be an important feature when objective measurements of IgE in the absence of other isotypes are desired, or when specific isotypes of antibody are measured without interference from other isotypes. A further implication of this embodiment is the removal of immune complexes of allergen, IgE and IgG because of the polyclonal nature of the immune response to a number of epitopes on the allergen surface. Removal of such complexes could decrease the number of asymptomatic specific IgE positive results, which is currently found with current classical allergy tests for the measurement of specific IgE. The absorption technique could also be extended to the removal of crossreactive antigens in the case of immunoassays for other analytes, or for the removal of interfering components (such as immune complexes as in certain disease conditions) and also where biologically active components or chemically interfering materials (such as proteases and other binding substances) need to be removed.

The mobile phase also simultaneously passes along the second flow path through the labelled immunoreactive material to the detection zone. During the initial ten minute separation of the plasma from the whole blood sample, the mobile phase also serves to rehydrate dried developer reagent, such as a labelled anti-human IgE antibody, in the second flow path.

After a specified period of time, typically ten minutes, the second phase of reaction is initiated by the physical movement of the detection zone from the first flow path to the second flow path. This process may be carried out manually or by other means. Now the active flow path is from the reservoir or mobile phase receiving zone through the rehydrated labelled antibodies into the detection zone. An important feature of the breaking of the flow of the first flow path is that there is little chance for the red cells from the blood sample to diffuse into the detection zone and thereby obscure the result on the detection filter.

The labelled immunoreactants pass through the detection zone as a bolus which serves two purposes:

(i) the concentration of the labelled immunoreactants in the detection means is increased hence increasing the reaction rate; and (ii) the bolus is followed by a zone of mobile phase which serves to clear the detection zone of remaining labelled immunoreactants thereby reducing any nonspecific binding and increasing the signal to background readings.

At the end of the detection means lies a sink which may or may not be always in contact with the detection means except during the second phase of the test whereby the detection means and the second flow path are in contact. This area serves as a sink for unreacted material and can thereby accumulate unreacted (excess) labelled immunoreactants thereby changing the visual appearance of the sink either directly in the case of particulate labels or indirectly through reaction of the labelled immunoreactants by a further developer. This enables the excess labelled immunoreactants to serve as a means of determining when the test is complete.

The movement of the detection means is a key feature. The detection means is clipped into the second flow path and importantly holds the filter at an angle to the surface of the detection means. The first flow path and second flow path are also inclined at a similar angle such as when the detection means is pulled from the first flow path, the detection means is forced against the second flow path, ensuring a good contact to allow continuity of the flow of the mobile phase and reactants it carries. The detection means may also contain a window through which the result of the test can be observed.

According to another feature of the present invention, an allergosorbent may be used. Due to the high sensitivity required for the detection of small amounts of allergen specific IgE compared to allergen specific IgG, and the fact that the IgE may be directed to only a small fraction of the allergosorbent, the properties of the substrate for binding the allergens should be highly efficient. The flow rate is also important, because too rapid a flow rate would result in too low a sensitivity. A plastics backed nitrocellulose membrane (SSLU, Schleicher and Schuell) with a pore size of 3 to 5 μm, or a Whatman 3 mm, has been found to be suitable for the determination of allergen specific IgE.

The apparatus according to the invention may be used for the detection of multiple allergen specific IgE rather than IgE towards a single allergen. For example, in the case of the embodiment according to the present invention with non-movable detection means, the rate of flow through the allergosorbent will be proportional to the length of the respective flow path. Hence the larger the panel of allergens tested, the longer will be the development time for a result to be observed.

The allergens may be applied to the nitrocellulose with a pen capable of dispensing aqueous allergen extracts at 1 $\mu$l per linear cm at concentrations ranging between 1 to 10 mg/ml in 50 mM Tris buffered saline pH7.4 (the protein concentration depending on the source of extract used). The nitrocellulose may then be allowed to dry at room temperature for 30 minutes. The excess reactive groups on the nitrocellulose may then be blocked for 1 hour with a Tris buffered saline solution containing 0.05% v/v Tween-20. A further wash with the above buffer may be performed for 15 minutes prior to allowing the membrane to dry at room temperature for 3 hours and then storing the desiccated material at 2 to 8° C.

It is preferred that the detection means comprises an immunoadsorbent. Many current immunoassay devices operate by the sample flowing through a zone of labelled immunoreactants downstream from the sample application zone, which immunoreactants bind specifically with the analyte if found to be present in the sample. The label constitutes the means by which the specific analyte is made detectable to the user. This labelled immunoreactant can be direct, for example, when bound to dyed latex particles, gold colloids or dye sols. The labelled immunoreactant may also be indirect, such as when the label is a biological enzyme that requires treatment with a substrate and chromogen prior to detection of the label, or when silver enhancer reagents are required before previously undetectable gold labels are rendered visible. The labelled immunoreactant may be free to move along with the mobile phase. The labelled immunoreactant-analyte complex, if present, moves downstream according to the flow initiated by the reservoir of mobile phase, towards an immunoadsorbent layer.

Here, for example, a further immunoreactant, again specific for the analyte (but to a different reactive group on the analyte) can bind to the labelled immunoreactant-analyte complex, downstream from the labelling zone. The presence of analyte in the sample can therefore be visualized by the accumulation of labelled complex at the site of the immunoadsorbent. In a further feature of the apparatus, depending on the nature of the labelled immunoreactants, the mobile phase may be water-based (e.g. a saline solution), it may contain a substrate and/or chromogen for an enzyme label, or it may contain a silver enhancer reagent (such as one commercially available suitable for the visualization of histological sections with colloidal gold reagents from Sigma-Aldrich Company) or one of the components of such a reagent when gold-labelled immunoreactants are used for detection (or indeed other detection agents).

The assay can be rendered more sensitive by the lateral flow of a silver enhancer solution. This allows the use of smaller gold colloids giving better penetration and resolution of the membrane but then enhanced by the deposition of metallic silver on the surface of the colloidal gold. This should be useful to the clinical laboratory where applications involving minute sample volumes are required or where ultra-sensitive detection systems are required for the simultaneous determination of multiple analytes from a minute sample. The gold conjugates may also be silver-coated prior to their inclusion within the apparatus according to the invention.

Such conjugates may be prepared by incubating a titered aliquot of gold labelled antibody (dialysed or suitably diluted to remove ions such as chloride), preferably 5 nm or less, with a reactive solution of silver enhancer for 5 to 10 minutes, followed by centrifugation and three washes with equal volumes of distilled water, to remove excess silver enhancer.

A positive result in such immunoassays using such pre-silver stained gold conjugates with silver-stained gold conjugate is represented by an intense black coloration at the binding site, thereby providing sensitivities many orders of magnitude greater than that of the original gold colloid. These silver-stained gold conjugates can be readily prepared and are stable in both liquid and dried form. Smaller gold conjugates of 5 nm or less are most appropriate for silver staining. The intensity of silver staining can be modulated by the concentration of reactants, removal of interfering salts, temperature (a reduction in temperature can be used to control the rate of reaction) and the type of labelling system used. These silver stained gold conjugates may also be of use where a passive immunoassay format is used, such as in classical protein and nucleic acid blotting.

In a further embodiment of the invention, there may be included an onboard control that indicates when the assay has been complete or successful. This control (or a further control) can also be used as a reference to the test result obtained with the specific analyte. Thus, by comparing the intensity of the reference with the test result, an indication as to whether the test result was positive or negative will be obtained. Hence, by means of a further apparatus that measures the intensity of the response, a quantitative measure could be achieved by comparing the activity of the reference with the test result.

Alternately, the device may also contain an electronic means of detecting the result, the termination of the test and audible or visible step-by-step instructions for performing the test. Inclusion of these electronic features would allow greater confidence of the user in performing the test correctly and reduce the requirement for the reading of instruction leaflets prior to use. For example, regions of the device could contain sensors that detect moistness of the flow paths thus determining the step the test is at during the processing of the sample. Such sensors could be linked to visual or audible displays of the processing step and indicate the next step. Such sensors in the detection zone could include densitometric measurements, that determine the amount of labelled antibody specifically bound by analyte in the detection zone in order to produce a quantitative result or a means of indicating when the detection means should be pulled to the developer position such as an audible warning or visual instruction or signal. The electronic sensor could also indicate when sufficient blood has been added to the sample receiving zone by, for example, the determination of the change in conductivity of the filters between the dry and wet state or when the ionic composition of the filter changes due to the addition of polar solvents or sample or by measuring a change in optical density such as that resulting from the addition of a colored sample (as is the case with a blood drop) by means of a photocell for example.

A further embodiment could include means for measuring the amount of sample added. This again could be done through electronic means as described above or more simply through the use of an integral capillary tube or similar that would "draw up" a fixed volume of sample into the device for the analysis.

The detector could also take the form of an electronic device where the physical properties of the solid phase to which the allergens are absorbed is changed by the binding of the labelled anti-human IgE antibodies to these zones when in the presence of the analyte ie allergen specific IgE.

The present invention therefore helps to eliminate common pitfalls in immunoassay technology associated with known apparatus.

Sequential assay also allows amplification of the assay system by the use of multiple additions of antibodies e.g. in the case of a sensitive allergy test, the first antibody may be a biotinylated anti-human IgE which is washed through by a gold-labelled anti-biotin second antibody which is readily visible to the naked eye when concentrated, in the form of a discrete reaction zone at the immunoadsorbent site.

The intermission of discrete wash steps common to routine sequential assays as performed in clinical laboratories is unnecessary for this format of the assay, because the capillary nature of the filters and membranes, as the first antibody is washed out with little reaction and mixing by the second antibody. The same can be said about the sample which is pushed out of the filter by the influx of the primary antibody.

A principal embodiment of the apparatus according to the invention is the circumvention of the requirement for discrete wash steps while still retaining a sequential immunometric assay format and is especially applicable for apparatus to be used in the home or doctor's office. This is achieved by the construction and, in the case of the embodiment with non-movable detection means, geometry of the conducting elements transporting the mobile phase. In contrast to known apparatus, it is a feature of the apparatus according to the invention that the sample can be applied to a region close to the immunoadsorbent. Mobile phase can then be applied upstream of the sample either by release from a compartment within the device or added from a separate container supplied as part of the apparatus. This circumvents the necessity for the mobile phase to enter the labelled immunoreactant zone before reaching the sample.

Therefore, due to a possible difference in flow characteristics of the two paths mentioned above, it is evident that arrival of the labelled immunoreactants much later at the immunoadsorbent than the initial analyte from the sample application point will effectively result in a sequential immunometric assay. This procedure allows the sequential format described, to take place without the requirement of a previous interaction with a labelled immunoreactant and without discrete wash steps or separate multiple applications of reagents by the user.

In a further embodiment of the invention, the number of paths need not be limited to two. A further increase in the number of paths of varying flow characteristics provides more flexibility with the testing system, allowing more complex chemistries to take place or facilitate enhanced washing steps if required, or chemical modifications steps or reaction with different labelled immunoreactants in turn on the solid phase. Nevertheless, the only requirement for the user, irrespective of the number of flow paths, is to provide a sample at the application point and then to initiate the flow of the mobile phase either from within the device or via an external container.

The most rapid path need not necessarily lead to the sample. The present invention could also be applicable in carrying out the immobilization of immunoreactants during operation of the apparatus, rather than immobilized immunoreactants being prepared by the manufacturer.

A sequential format is particularly useful when monoclonal antibodies are unavailable. In general, polyclonal antibodies can potentially give greater sensitivity in immunoassays and can be more stable when labelled than monoclonal antibodies. It is important when using a non-sequential assay device, as described previously, that the labelled antibody is specific for one epitope while the immobilized immunoreagent is specific for a spatially distinct distant epitope. However, in some cases this would preclude the use of polyclonal antibodies because of the possibility of reaction with the epitopes recognized by the immobilized immunoreactant on the immunoadsorbent, thereby effectively masking the epitopes to the immunoadsorbent, reducing binding and hence reducing the signal.

A sequential assay format eliminates these problems and is particularly useful when the analyte is an immunoglobulin or when only polyclonal antisera are available. The immunoadsorbent is usually immobilized allergen extract. However, specific allergen assays may also be conducted by using an immobilized anti-human IgE antibody and labelled allergens. The multiple simultaneous detection of IgE and IgG antibodies directed against an allergen could also be performed by adapting this method using labelled allergens. In this method, for example, the detector may comprise two zones:

(a) a zone containing an immobilized anti-IgE antibody; and (b) an immobilized IgG binding reagent such as protein A or anti-IgG antibody.

Unlike many immunometric assays where the immunoadsorbent is a preparation of purified antibody, for allergen extracts they are usually complex mixtures of a multitude of proteins. For example, house-dust mite extracts contain many antigens and allergens each reacting differentially with blood samples from different individuals. Here, previous reaction of the IgE present in a capillary blood sample with labelled anti-human IgE antibodies, as would occur using conventional devices for home/office testing, can possibly inhibit interactions with the allergosorbent solid phase due to the orientation of the anti-IgE/IgE complex interfering with the binding of such complex to the immunoadsorbent. A particular feature of most laboratory based allergy tests is that they adopt a sequential assay format, thus circumventing this problem of steric hindrance by allowing the IgE in the patient sample to bind to the allergen solid phase first. Then, a polyclonal labelled anti-human IgE antibody preparation can be used in excess to ensure quantitative estimation of the specific IgE bound.

A major advantage of the use of the sequential format in a diagnostic device is in the case of celiac disease. Here the presence of Immunoglobulin A (IgA) antibodies against the cereal protein gliadin in the blood and some other body fluids, for example saliva, is an indication of celiac disease. However, the fraction of gliadin specific IgA compared to total IgA in blood samples from individuals with celiac disease can be very small. This means that in order to detect gliadin specific IgA, a sensitive detection system is required together with a large sample volume, if the signal obtained with a sample containing gliadin specific IgA antibodies is to be distinguished from blood samples that are not. The increase in the sample size, corresponds to an increase of total IgA respectively, which has the result that existing non-sequential assays could be too insensitive, as there is a possibility that due to the increased sample volume and total IgA levels, that the high levels of non-gliadin specific IgA could potentially swamp out the detection of the gliadin specific IgA by saturation of the labelled anti-human IgA antibodies.

Thus the use of a sequential assay, of first allowing the human anti-gliadin specific IgA to bind to immobilized gliadin immunoadsorbent, then reacting in a separate stage thereafter with the labelled anti-human IgA, will result in a more specific, sensitive and reduced possibility of false negative assays which may have been caused by saturation of the assay system with the non-gliadin specific IgA found in the blood sample. It is also possible that the mobile phase could be used to cause a slow or gradual release of labelled reactants from a matrix which would act in concert with the sequential assay format described above to provide an even clearer separation of immunoreactants during operation of the device. For example, in the case of specific IgA against gliadin, the assay would be relatively insensitive if non-specific IgA was not removed prior to detection with an anti-IgA label, which in conventional laboratory based immunoassays is circumvented by a sequential assay format which incorporates a wash step to remove non-specific immunoreactants prior to the addition of labelled antibody. However in a diagnostic apparatus designed for use in the home or the office, discrete wash steps are inconvenient and cumbersome and a possible source of error.

The result depends on a number of factors including; the manual intensity of washing performed by the operator, the reagents used for the wash step may differ, especially if tap water is advised e.g. contaminants, microbial, particulates, force and temperature. To circumvent the requirement for a wash step, the apparatus should contain where necessary means for the removal of non-specific reactants. It is therefore a further embodiment of the apparatus described here that, if necessary and depending on the analyte to be measured, means for the slow release or desorption of the labelled immunoreactants should be an integral part of the operation. In practice, such a slow release mechanism could take the form of a mechanical barrier, for example, a gel or encapsulating material, or chemical means such as adsorption to a charged matrix such as an ion-exchange material or affinity adsorbed by a specific property of binding of the labelled reactant for an immobilized ligand and desorbed by a suitable change in ionic strength, hydrogen ion concentration, or addition of compounds that antagonize ligand-reactant binding. The slow release in the latter case may be mediated by the immobilized labelled analyte being surrounded by an environment that promoted binding where the mobile phase antagonizes this binding. Essentially this sets up a gradient through the matrix housing the adsorbed labelled reactant, until eventually at a particular gradient strength, the adsorbed material will begin to be released. Prior to the release of the labelled reactant, the passage of the mobile phase through the sample adsorption zone will allow the specific binding of the human antibody specific for the immobilized ligand in the detection zone without the interference from the labelled reactants with non-specific analytes.

Translocation of the mobile phase including the immunoreactants may be achieved by movement along chambers or channels formed by the body of the apparatus itself, specific capillary tubing, channels and troughs or from compartments with flow limiting orifices or movement along wicks by capillary action. Such wicks may be of synthetic or natural materials. The choice of material suitable for the translocation must be such that passive adsorption of the immunoreactants onto these conducting elements does not occur; the material can be treated to prevent deposition of the immunoreactants on the surface of the conducting elements. If required, the materials used for the conducting elements can either be treated before the device is assembled and/or during operation of the device. For example, blocking components such as irrelevant proteins, polymers, detergents and other routinely used blocking reagents common to the practice of immunoassay design should not be present. The capillary elements main purpose is to provide a flow path for the mobile phase and to connect sections of the apparatus that contain immunoreactants or detecting agents that need to be separate prior to conducting the test, and to allow reagents to be added to the immunoadsorbent at different times. Viscosity modifiers can be used to adjust the rate of translocation together with the flow characteristics of the conducting elements. Regions of the conducting elements may also be modified to perform chemical/immunological interactions with the mobile phase and its contents at that particular region of the apparatus. The choice of material for the conducting elements may therefore be of great importance for the successful operation of the apparatus.

An important embodiment by which a sequential assay may be performed by a single addition of mobile phase at the start of the operation of the apparatus is to have a number of separate conducting elements. In such a system, conducting elements emerge from a single reservoir which may or may not contain chemically or immunologically active constituents as is required by the particular analyte to be detected. By allowing a single reservoir to feed a number of conducting elements, this allows different reagents to be applied to the test zone at various positions and at controlled intervals of time. That is, differentially varying the flow characteristics of each conducting element will result in different flow rates and hence arrival of various reagents at different times to the immunoadsorbent. The flow of the mobile phase and reactants through a particular conducting element could also be modulated by the composition of the conducting element matrix and also by the addition of flow modifiers to each of the conducting elements to change the viscosity. An important embodiment of this invention is the circumvention of the requirement of detection agent modulators. For example, reducing agents may be used to prevent premature chromogen formation when using horseradish peroxidase labelled immunoreactants.

The apparatus according to the invention may permit an unlimited number of additions of reagents even though they are all initiated from a single reservoir of mobile phase. This will greatly enhance the potential usefulness of such single step apparatus as the problem of sequential addition of reagents can be overcome. The multiple conducting element system circumvents the requirement for discrete wash steps in such apparatus, allowing the measurement of a wider dynamic range of analytes and concentrations, while eliminating the possibility of high dose hook effects which can occur in some non-sequential immunometric assays, that do not have a wash step incorporated to remove unbound analyte to the solid phase immobilized immunoreactant.

The multiple conducting elements can be arranged as a sheet in two dimensions or as a three dimensional structure where more than one "sheet" of conducting elements can be separated by "insulating" layers of material forming a sandwich of conducting elements. For some analytes, the optimal configuration for the apparatus may be a combination of the two formats especially if more than one analyte is to be detected at a time. Either way, such a design would allow a complex series of chemical and immunoreactions to occur separated in time and distance but ultimately brought together in the correct sequence at the detection zone to give the required result.

BRIEF DESCRIPTION OF THE DRAWINGS

An immunoassay analytical test apparatus for allergy diagnosis according to the present invention is shown schematically in FIGS. 1 to 4 of the accompanying drawings, which are by way of example only. In the drawings.

Figure 1:
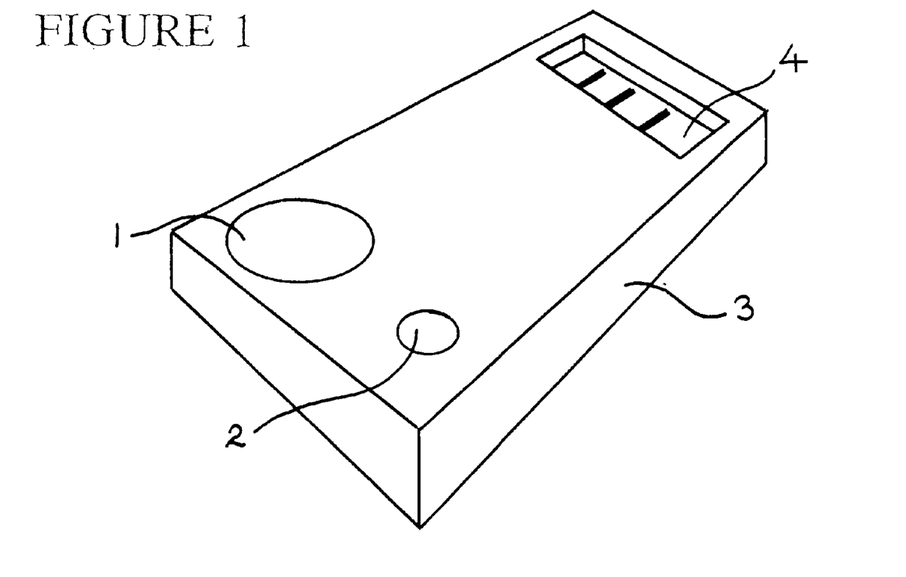
FIG. 1 shows the outward appearance of an immunoassay apparatus.

FIG. 1 shows the outward appearance of the apparatus (FIG. 1) includes a receptacle for receiving the mobile phase (1), a zone for the addition of the users sample containing the analyte (2), which may also be incorporated in (1), both (1) and (2) being near the surface of the apparatus housing (3). The detection zone (4) is situated within the housing (3) and may be protected by a transparent window. The detection zone contains the immunoadsorbent on which the result is observed.

Figure 2:
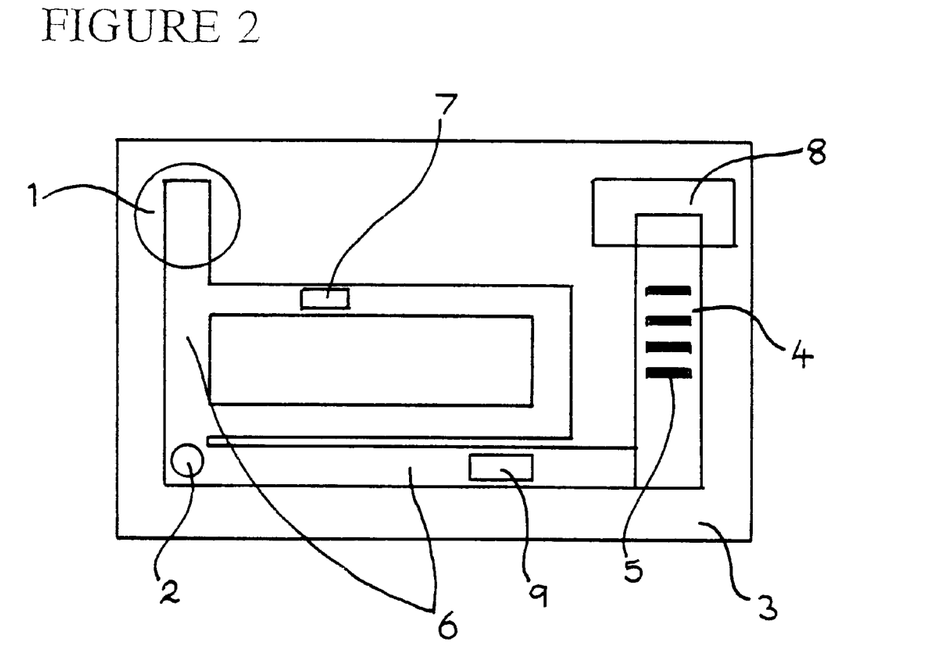
FIG. 2 shows an immunoassay apparatus according to the second embodiment of the present invention, having therein a longer flow path for the labelled immunoreactive material relative to the flow path for the analyte.

An important embodiment of the apparatus of FIG. 2 is the construction of the conducting elements. In principle, the apparatus consists of conducting elements of various path lengths and flow characteristics. The most rapid and direct path for the mobile phase arises at the point of the reservoir application (1) where the mobile phase is added and leading to the sample application zone (2) situated on or near the immunoadsorbent. The geometry of the solid phase, together with the materials used to construct the reservoir (1), sink (8), conducting elements (6) and immunoadsorbent (4) are designed to potentiate flow towards the sink (8). The sample application zone leads to the immobilized reactant on the immunoadsorbent (5) via a filter 9 for removing non-IgE components. The labelled antibody zone (7), is freely mobile within the conducting elements when mobile phase from the reservoir is present and may lead directly to the immunoadsorbent or pass through the sample zone as indicated in FIG. 2. The time taken for the labelled reactants to reach the immunoadsorbent is longer than for the sample. This configuration is simple to manufacture from available materials and will result in a sequential assay format essentially due to the difference in arrival times of the sample and labelled antibody or further reagents at the immobilized immunoreactant zone.

Figure 3:
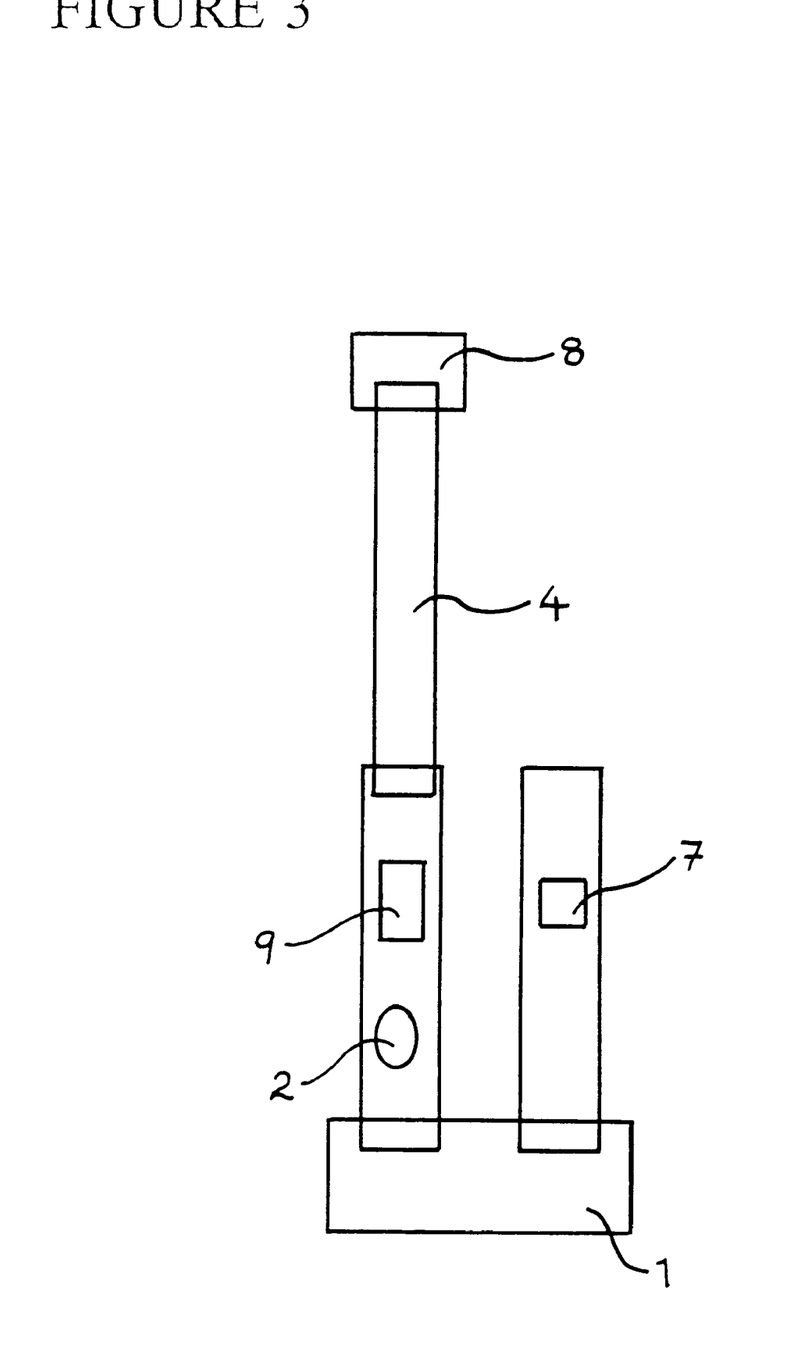
FIG. 3 shows the apparatus according to the first embodiment of the present invention, having therein a movable detection zone which is shown in connection with the first flow path.

Referring to FIG. 3, a further embodiment of the present invention is represented by a reservoir (1) comprising the mobile phase, a first flow path comprising a sample application zone (2), a filter (9) for removal of non-IgE components and a second flow path comprising a labelled antibody zone (7). There is further provided a movable detection zone (4), comprising a sink (8). The detection zone (4) is shown in connection with the first flow path.

Figure 4:
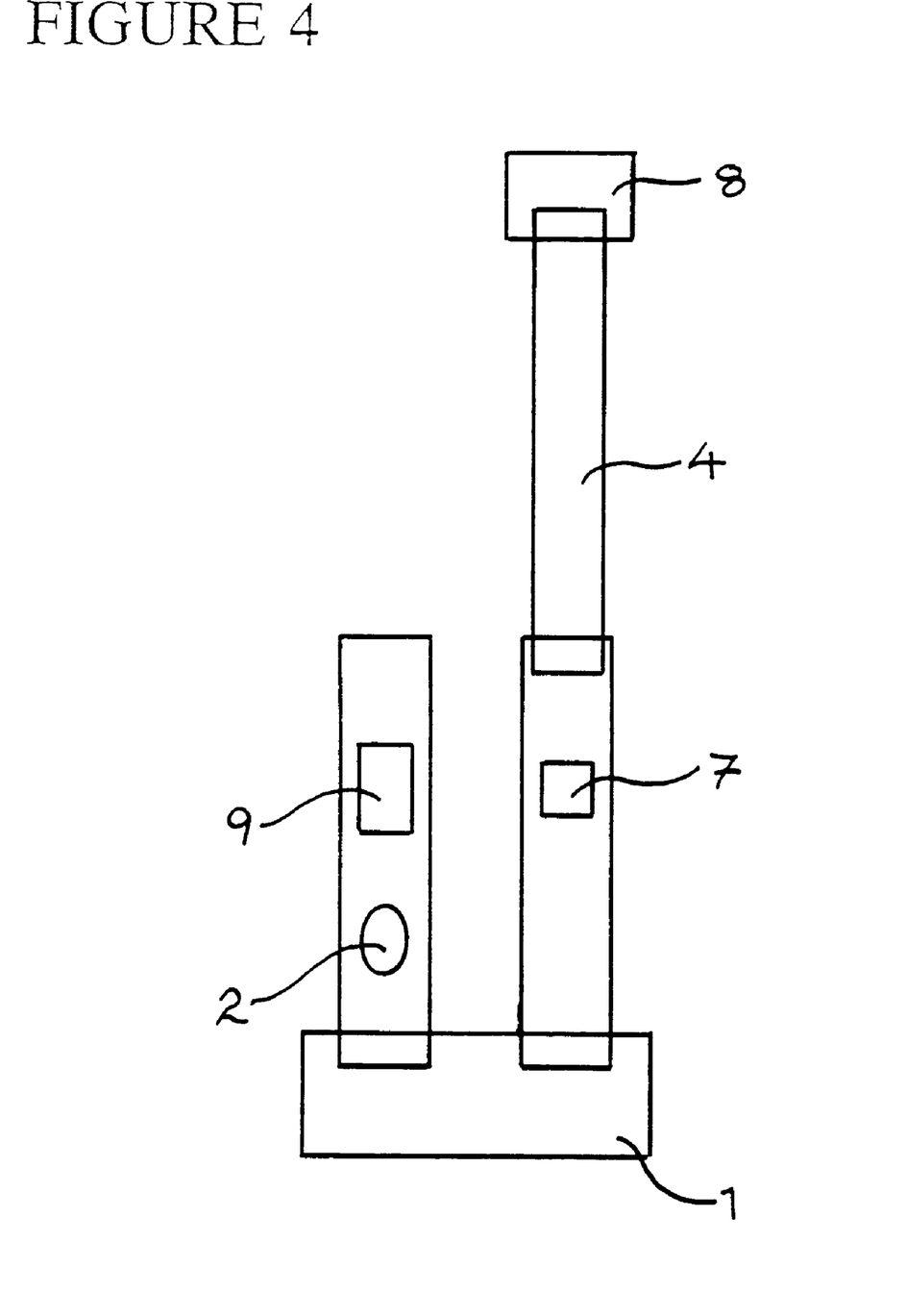
FIG. 4 shows the apparatus of FIG. 3 with the detection zone in connection with the second flow path.

Referring to FIG. 4, the apparatus of FIG. 3 is shown with the detection zone (4) in the second flow path.

There need not be limitation to two conducting elements as illustrated but there may be a multitude whenever a more complex chemistry of reactants is desired. This arrangement can also be simply extrapolated to form a three dimensional structure where the conducting elements of various physical properties are stacked one upon another prior to adjoining the immunoadsorbent.

EXAMPLES

The invention will now be illustrated in more detail with reference to the following worked examples.

Example 1

A piece of Schleicer and Schuell plastic backed nitrocellulose (SSLU) 5 mm×60 mm was prepared as described above. Three lines of allergen were imprinted within the nitrocellulose 10 mm apart representing Timothy Grass/Cocksfoot Mixed allergens (2 mg/ml), Cat allergens (10 mg/ml, Bayer) and Dermatophagoides pteronyssinus extract (20 mg/ml, Smithkline Beecham). A piece of GF/A glass fiber filter paper (Whatman, 5 mm×35 mm) was attached to the proximal end of the nitro-cellulose and a piece of CHR17 (Whatman, 5 mm×40 mm) to the distal end by solvent adhesive to a plastics support, with a 5 mm overlap onto the nitro-cellulose surface. A 25 $\mu$l sample of three serum pools RAST grade 3 to 4 positive for either grass pollen, cat or mite allergens or a normal goat serum pool were spiked with an equal volume of fresh human normal donor red blood cells, and added as a 50 $\mu$l aliquot to the centre of the GF/A filter. Once absorbed, the free end of the filter was placed in contact with 200 $\mu$l of 50 mM Tris buffered saline pH7.4 containing 0.5 $\mu$g of biotinylated Goat anti-human IgE (Vector Laboratories) and allowed to absorb for 1 hour. The free end of the filter was then placed in contact with 300 $\mu$l of the above buffer containing 30 $\mu$l of gold (40 nm) labelled Goat anti-biotin (British Biocell International) and allowed to absorb. After 30 minutes positive results were observed by the presence of pink/red lines corresponding to the representative allergens from each of the serum pools, except for the normal goat serum which served as a negative control where no lines were visible for any of the allergens tested.

Example 2

A piece of Schleicer and Schuell nitro-cellulose (5×30 mm) was impregnated with mite extract as described above. A piece of GF51 (Schleicher and Schuell, 5×25 mm) was attached to the nitro-cellulose with a 5 mm overlap and both components fixed by adhesive to a plastics support. A 25 $\mu$l aliquot of RAST grade 4 positive serum from a house dust mite positive patient pool was then added to the GF51 to a region previously impregnated with 0.5 $\mu$g of biotinylated goat anti-human IgE in 10 $\mu$l of Tris buffered saline. A 100 $\mu$l aliquot of gold(40 nm) labelled goat anti-biotin in Tris buffer containing 1% w/v bovine serum albumin was then added dropwise to the GF51 filter. A positive band corresponding to reactivity of the serum with the mite extract was observed within 30 minutes.

The reactants, except for the mobile phase, are probably best stored within the apparatus in a solid form to enhance stability, as it is desirable for the apparatus to be stored at ambient conditions. Biological components are notorious for degradation in solution whereas storage in a dried state or chemically coupled to some matrix confers some protection to their innate lability. Another problem with biological materials (especially proteins) is their tendency to adsorb non-specifically to matrix surfaces such as glass, paper and plastics. These interactions have to be minimized if the reactants are to be of any use in the apparatus. One method is to pretreat the matrix holding the reactants with a non-specific blocking reagent as described above. Another method may be to chemically bind them to the solid phase but to include a releasing agent that releases the reactant from the solid phase into the mobile phase. One way to add the reactants is in a liquid form onto the non-adsorbent matrix and then to remove the liquid thereby drying as a film. The reactants could also be added in the form of a gel (such as agarose or gelatin), or simply dried into the matrix with a detergent. The components of the device also contain preservatives to help prevent deterioration of the product by microbial organisms and to help protect against adverse environmental conditions, for example, temperature light and humidity.

What is claimed is:

1. An immunoassay analytical test apparatus for screening for the presence of an analyte in a sample of body fluid obtained from an animal subject, said apparatus comprising:
   a) a first flow path including a sample receiving zone for receiving said sample;
   b) a second flow path including non-immobilized labelled immunoreactive material that can interact with said analyte;
   c) a mobile phase receiving zone for receiving a mobile phase, said mobile phase receiving zone being in communication with said first and second flow path; and
   d) a detection zone including an immunoadsorbant for binding said analyte when said analyte is present in said sample; wherein
      said first flow path allows flow of said sample in said mobile phase from said sample receiving zone to said detection zone where said analyte present in said sample is allowed to substantially bind with said immunoadsorbant; and said second flow path allows flow of said labelled immunoreactive material in said mobile phase to said detection zone without passing through said sample receiving zone; said first and second flow paths being arranged and configured such that said labelled immunoreactive material arrives at said detection zone substantially after said sample has reached said detection zone, whereby said labelled immunoreactive material is allowed to substantially bind to said analyte when said analyte has bound to said immunoadsorbant, so as to provide an indication of the presence of said analyte in said sample.

2. An immunoassay analytical test apparatus for screening for the presence of an analyte in a sample of body fluid obtained from an animal subject, said apparatus comprising:
   a) a first flow path including a sample receiving zone for receiving said sample and a zone of non immobilized capture material, wherein said zone of non-immobilized capture material can interact with said analyte;
   b) a second flow path including non-immobilized labelled immunoreactive material that can interact with said analyte;
   c) a mobile phase receiving zone for receiving a mobile phase, said mobile phase receiving zone being in communication with said first and second flow path; and
   d) a detection zone including immunoadsorbant for binding said capture material; wherein
      said first flow path allows flow of said mobile phase through said sample receiving zone and said zone of non-immobilized capture material so as to obtain a mixture wherein said capture material can bind with said analyte present in said sample of body fluid; said mixture being allowed to flow along said first flow path to said detection zone where said capture material binds with said immunoadsorbant; and said second flow path allows flow of said labelled immunoreactive material in said mobile phase to said detection zone; said first and second flow path being arranged and configured such that said labelled immunoreactive material arrives at said detection zone substantially after said mixture has reached said detection zone, whereby said labelled immunoreactive material is allowed to substantially bind with said analyte when said analyte has bound with said capture material bound to said immunoadsorbant, so as to provide an indication of the presence of said analyte in said sample.

3. An immunoassay analytical test apparatus for screening for the presence of allergen-specific IgE in a sample of body fluid obtained from an animal subject, said apparatus comprising:
   a) a first flow path including a sample receiving zone for receiving said sample;
   b) a second flow path including non:immobilized labelled allergen that can interact with said allergen specific IgE;
   c) a mobile phase receiving zone for receiving a mobile phase, said mobile phase receiving zone being in communication with said first and second flow path; and
   d) a detection zone including immunoadsorbant for binding said allergen-specific IgE when present in said sample; wherein
      said first flow path allows flow of said sample in said mobile phase from said sample receiving zone to said detection zone where said allergen-specific IgE present in said sample is allowed to substantially bind with said immunoadsorbant; and said second flow path allows flow of said labelled allergen in said mobile phase to said detection zone; said first and second flow paths being arranged and configured such that said labelled allergen arrives at said detection zone substantially after said sample has reached said detection zone, whereby said labelled allergen is allowed to substantially bind to said allergen-specific IgE, when said allergen-specific IgE has bound to said immunoadsorbant, so as to provide an indication of the presence of said allergen-specific IgE in said sample.

4. The apparatus according to claim 3, wherein:
   said first flow path includes a matrix or filter for removal of non-IgE components.

5. The apparatus according to claim 4, wherein:
   said filter or matrix is provided between said sample receiving zone and said detection zone.

6. An apparatus according to claim 4, wherein:
   said filter or matrix is provided in said sample receiving zone.

7. An immunoassay analytical test apparatus for screening for the presence of an analyte in a sample of body fluid obtained from an animal subject, said apparatus comprising:
   a) a first flow path including a sample receiving zone for receiving said sample and a filter arranged to separate components of said sample, said filter selected from a group consisting of:
      a blood filter arranged to permit plasma to pass while capturing other blood constituents; and
      a matrix for the removal of material other than said analyte;
   b) a second flow path including non-immobilized labelled immunoreactive material that can interact with said analyte;
   c) a mobile phase receiving zone for receiving a mobile phase, said mobile phase receiving zone being in communication with said first and second flow paths; and
   d) a detection zone including an immunoadsorbant for binding said analyte present in said sample; wherein said first flow path allows flow of said sample in said mobile phase from said sample receiving zone to said detection zone where said analyte present in said sample is allowed to substantially bind with said immunoadsorbant; and said second flow path allows flow of said labelled immunoreactive material in said mobile phase to said detection zone; said first and second flow paths being arranged and configured such that said labelled immunoreactive material arrives at said detection zone substantially after said sample has reached said detection zone, whereby said labelled immunoreactive material is allowed to substantially bind to said analyte, when said analyte has bound to said immunoadsorbant, so as to provide an indication of the presence of said analyte in said sample.

8. The apparatus according to claim 7, wherein:
said filter is provided between said sample receiving zone and said detection zone.

9. The apparatus according to claim 7, wherein:
said filter is provided in said sample receiving zone.

10. An immunoassay analytical test apparatus for screening for the presence of an analyte in a sample of body fluid obtained from an animal subject, said apparatus comprising:

a) a first flow path including a sample receiving zone for receiving said sample;

b) a second flow path including non-immobilized labelled immunoreactive material that can interact with said analyte;

c) a mobile phase receiving zone including a store of releasable mobile phase, said mobile phase receiving zone being in communication with said first and second flow paths; and d) a detection zone including an immunoadsorbant for binding said analyte present in said sample; wherein
said first flow path allows flow of said sample in said mobile phase from said sample receiving zone to said detection zone where said analyte present in said sample is allowed to substantially bind with said immunoadsorbant; and said second flow path allows flow of said labelled immunoreactive material in said mobile phase to said detection zone; said first and second flow paths being arranged and configured such that said labelled immunoreactive material arrives at said detection zone substantially after said sample has reached said detection zone, whereby said labelled immunoreactive material is allowed to substantially bind to said analyte, when said analyte has bound to said immunoadsorbant, so as to provide an indication of the presence of said analyte in said sample.

* * * * *